US005638170A

United States Patent [19]
Trinka et al.

[11] Patent Number: 5,638,170
[45] Date of Patent: Jun. 10, 1997

[54] PUNCHED CARRIER SPECIMEN SAMPLE PROCESSOR

[75] Inventors: Robert F. Trinka, Norwalk, Conn.; Philip J. Farrelly, Short Hills, N.J.

[73] Assignee: Hudson Control Group, Inc., Springfield, N.J.

[21] Appl. No.: 255,315

[22] Filed: Jun. 7, 1994

[51] Int. Cl.⁶ ............................. G01N 21/01; G01N 1/04
[52] U.S. Cl. ........................ 356/244; 356/36; 83/167; 73/864.41
[58] Field of Search ........................ 356/244, 246, 356/36; 422/99, 100, 104, 66; 435/287, 292; 73/864.41, 864.43, 864.44, 864.45; 83/167, 684

[56]     References Cited
         U.S. PATENT DOCUMENTS

| 3,430,415 | 3/1969 | Phillips | 73/864.41 |
| 3,921,459 | 11/1975 | Willett | 73/864.41 |
| 4,341,735 | 7/1982 | Seifried | 73/864.44 |
| 4,682,891 | 7/1987 | de Macario et al. | 356/246 |
| 4,729,661 | 3/1988 | Bell | 356/246 |
| 5,290,513 | 3/1994 | Berthold et al. | 356/246 |

*Primary Examiner*—Hoa Q. Pham
*Attorney, Agent, or Firm*—Rohm & Monsanto

[57]     ABSTRACT

A dried sample processor employs a loader which reads unique identification data from a carrier web, and supplies such data to a computerized controller. The carrier web is then brought to a punch arrangement which punches a specimen sample therefrom and deposits same into a well of a microtiter array. The microtiter array and the wells therein are moved into registration with the punch hole of the punch unit under the control of the computerized controller. The correlated carrier web identification data and the address of the well in the microtiter plate are displayed as graphical information on a computer monitor, and made available to other components of a computerized laboratory.

17 Claims, 3 Drawing Sheets

PUNCHED CARRIER SPECIMEN SAMPLE PROCESSOR

BACKGROUND OF THE INVENTION

1. FIELD OF THE INVENTION

This invention relates generally to systems for processing samples obtained from a carrier material, and more particularly, to apparatus and method for processing samples which are punched out of a carrier web.

2. DESCRIPTION OF THE RELATED ART

In the field of substance testing, as would be the case in testing blood samples, numerous time-consuming functions must be performed, and a high degree of record keeping accuracy is required. One approach to resolving some of the problems associated with large scale substance testing involves the impregnation of an absorbent material, such as a blotter paper, with the substance desired to be tested. Upon drying, specimen samples are created from the carrier material, such as by mechanical punching equipment, and the samples are then subjected to a test environment.

This known approach to substance testing suffers from a number of disadvantages, not the least of which is that once the specimen samples are created, there is no easy way to trace back the specimen sample to its origin. Thus, in the case of blood testing, a specimen sample created in accordance with the known systems could not readily be traced back with accuracy to the individual who supplied the sample, unless the location of the specimen sample along the testing process was maintained by a human operator.

In addition to the foregoing, the known arrangements are relatively slow in their operation and do not provide the capacity for storing the sample specimen for testing at a later date. Accordingly, there is need for a simple and inexpensive system for producing specimen samples and quickly organizing them for testing while retaining an accurate record identifying each specimen sample. In addition, there is a need for a system which permits the specimen samples to be retained prior to testing, as might be the case where sample collection and sample testing occur at different facilities.

It is, therefore, an object of this invention to provide a system wherein sample specimens are obtained from a carrier material and a record is maintained whereby each sample specimen can be traced back to its origin.

It is another object of this invention to provide a system for processing large numbers of specimen samples, such as dried blood samples.

It is also an object of this invention to provide a system wherein specimen samples are collected and organized while permitting a delay prior to chemical testing.

SUMMARY OF THE INVENTION

The foregoing and other objects are achieved by this invention which provides, in a first aspect thereof, a loader arrangement for forming specimen samples from a sample carrier web and loading same into respective compartments of a two-dimensional array of the compartments. Each of the compartments has an opening, the openings being substantially co-planar with a compartment opening plane. In accordance with the invention, there is provided a punch arrangement for punching out a specimen sample from a carrier web. The punch arrangement has a female punch portion arranged on a first plane, having a punch hole therethrough. A punch rod portion is arranged to travel in a first direction of travel through and substantially orthogonal to the sample carrier web and the punch hole, whereby a specimen sample is punched out of the carrier web. A controllable array carrier moves the array of the compartments along first and second axes of motion. A controller controls the controllable array carrier such that predetermined ones of the compartments are moved into registration with the punch hole of the punch arrangement.

In one advantageous embodiment of the invention, the punch rod is arranged to travel in the first direction of travel beyond the punch hole and beyond the compartment opening plane, such that the punched out specimen sample is urged in the first direction of travel and deposited in a predetermined one of the compartments which is in registration with the punch hole. The punch rod portion of the punch therefore serves the dual purpose, in this embodiment, of cooperating with the punch hole for producing a specimen sample, and depositing the specimen sample in the compartment.

In a specific embodiment, the specimen sample has a size characteristic which is larger than a corresponding size characteristic of the compartment into which it is deposited. Thus, the punch rod portion urges the specimen sample into the specimen compartment to achieve an interference fit. This prevents the specimen sample from being easily displaced or removed form its intended compartment. Other embodiments of the invention, of course, do not require the interference fit noted herein. In such other embodiments, testing or other fluids deposited into the compartment will flow more readily around the specimen sample.

In a preferred embodiment of the invention, the sample carrier web is provided with a unique identification code. The loader arrangement is provided with a code reader connected to the controller for conducting sample carrier web identification data thereto. The unique identification code may be, in certain embodiments, in the form of a bar code, and the code reader is a bar code reader having a conventional configuration. The controller may be provided with a data port for issuing information corresponding to the identification of the sample carrier. This information may be provided to other systems in a laboratory to achieve fully automated record keeping.

In addition, the controller, which may be a computer, is provided in certain embodiments, with a memory capacity for storing correlation data corresponding to a correlation between the sample carrier identification data and the compartment location data which identifies the particular compartment in the two-dimensional array of the compartments. In some embodiments, the correlation data may be presented on a computer monitor which provides a graphical user interface, and therefore, the correlation data is graphically depicted.

In accordance with a further aspect of the invention, a loader arrangement forms specimen samples from a sample carrier web and loads same into respective compartments of an array of compartments in a micro well plate. In accordance with the invention, a punch arrangement is provided for punching out a specimen sample from the carrier web. The punch is provided with a punch hole and a punch rod, the punch rod being arranged to travel through the sample carrier web and the punch hole so as to produce a punched out specimen sample from the web. A controllable array carrier moves the micro well plate along first and second axes of motion substantially orthogonal to the travel of the punch rod. Additionally, a controller controls the motion of the controllable array carrier whereby a predetermined compartment of the micro well plate is moved into registration with the punch hole of the punch.

In accordance with a specific illustrative embodiment of this further aspect of the invention, there is further provided an identification arrangement coupled to the controller for producing a signal which corresponds to the identification of the sample carrier web. The identification arrangement is, in one embodiment, a reader which reads an identification code on the sample carrier web.

In a further embodiment, the controller controls the motion of the controllable carrier array such that the micro well plate is moved between a first region wherein the predetermined compartment of the micro well plate is moved into registration with the punch hole of the punch, and a second region where the micro well plate is to be replaced. Thus, the controller functions to control the motion of the controllable carrier array such that the micro well plate is moved within the first region so as to enable the loading of the compartments, and from the first region to a second region where the micro well plates is accessible for removal and replacement.

In accordance with a method aspect of the invention, a method of processing specimen samples form a sample carrier web includes the following steps:

controlling the motion of an array carrier for moving a micro well plate along first and second axes of motion;

punching out a specimen sample from the carrier web with a punch arrangement having a punch hole and a punch rod, the punch rod being arranged to travel through the sample carrier web and the punch hole in a direction of motion substantially orthogonal to the first and second axes of motion of the micro well plate; and urging the specimen sample by means of the punch rod into a predetermined micro well of the micro well plate, the predetermined micro well being moved into registration with the punch rod during said step of controlling.

In one embodiment of this method aspect of the invention, there is further provided the step of repeating said steps of controlling, punching out, and urging for different ones of the micro wells of the micro well plate. In a further embodiment, the step of urging includes the additional step of driving the specimen sample into the predetermined micro well of the micro well plate to achieve an interference fit of the specimen sample therein.

As previously noted, the step of controlling includes the step of controlling further the motion of the array carrier between a micro well loading region and a micro well plate replacement region.

In a highly advantageous embodiment of this method aspect of the invention, there is provided the further step of reading a carrier web identification symbol for identifying the carrier web uniquely. The identity of the carrier web is correlated with a respectively associated micro well of the micro well plate. Such identification of the carrier web is achieved, in some embodiments, by reading a bar code printed on the carrier web.

BRIEF DESCRIPTION OF THE DRAWING

Comprehension of the invention is facilitated by reading the following detailed description, in conjunction with the annexed drawing, in which.

DETAILED DESCRIPTION

Figure 1:
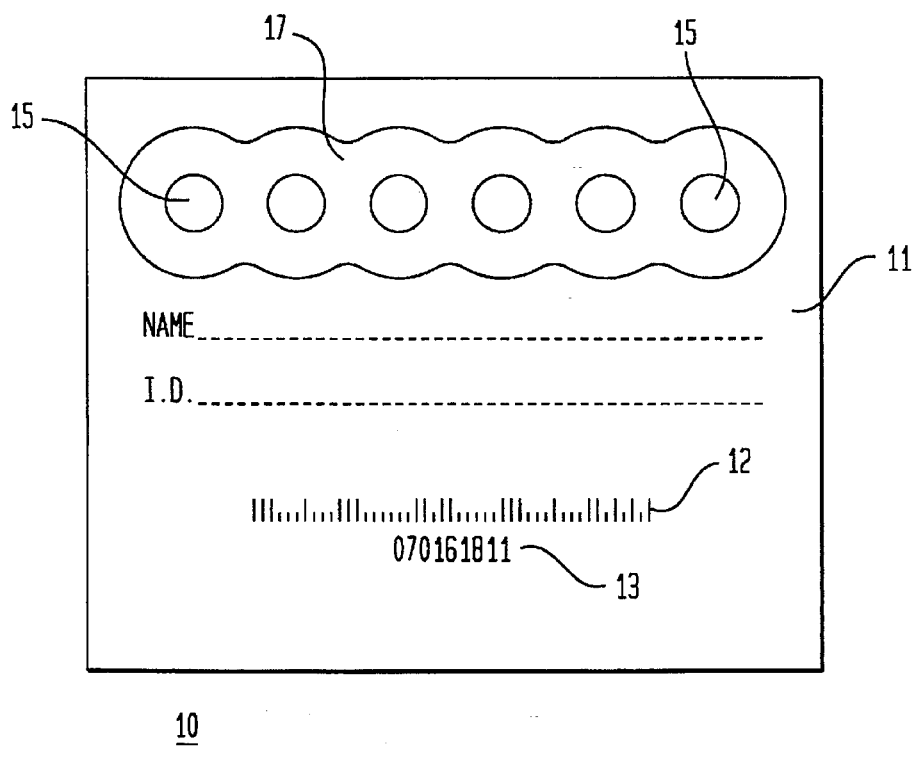
FIG. 1 is a representation of a carrier web shown to be impregnated with a substance to be tested.

FIG. 1 is a plan view of a carrier web 10 which may be formed of a blotter paper which readily absorbs a fluid material to be tested. As shown, carrier web 10 has printed thereon a region 11 for writing in a name or other identification information. The carrier web is further provided with a machine readable code 12 printed thereon, and may further contain a human readable identification code 13. In a preferred embodiment, machine readable code 12 and human readable code 13 are unique to the particular carrier web.

The carrier web is shown to have printed thereon a plurality of O-shaped markings 15 which assist the user in determining where the carrier web is to be punched, to produce specimen samples (not shown in this figure). The region where O-shaped markings 15 is printed is saturated with a fluid to be tested, such as blood 17, which is permitted to dry thereon prior to formation of the specimen samples. In this specific illustrative embodiment, the region of dried blood 17 is punched with a diameter which will produce an interference fit when the punch-outs (not shown in this figure) are deposited in respective wells, or compartments, of a microtiter plate 20.

Figure 2:
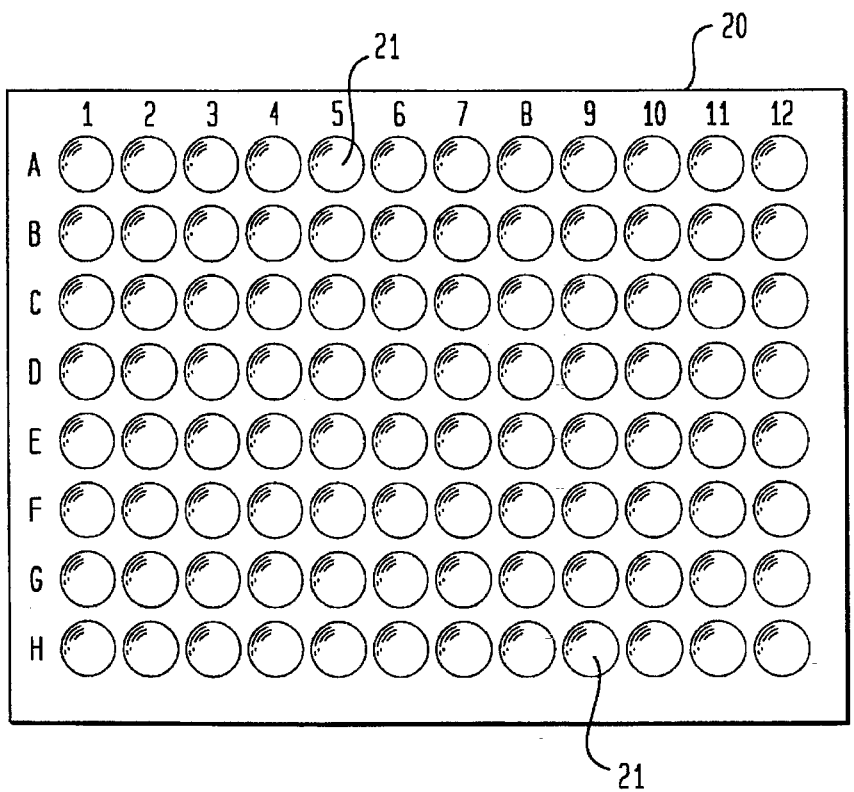
FIG. 2 is a plan view of a microtiter plate having an array of compartments into which are deposited specimen samples punched out of the carrier web of FIG. 1.

FIG. 2 is a plan view of a microtiter plate 20 showing an array of wells 21. In this specific embodiment, the array consists of eight rows (A–H) by twelve columns. In a practical embodiment of the invention, the microtiter plate is dimensioned approximately 3.25 inches high by approximately 5 inches wide, by approximately 0.6 inches deep, each well is shown to be configured substantially cylindrically, having a depth of approximately 0.4125 inches, and a diameter of approximately 0.26 inches.

Figure 3:
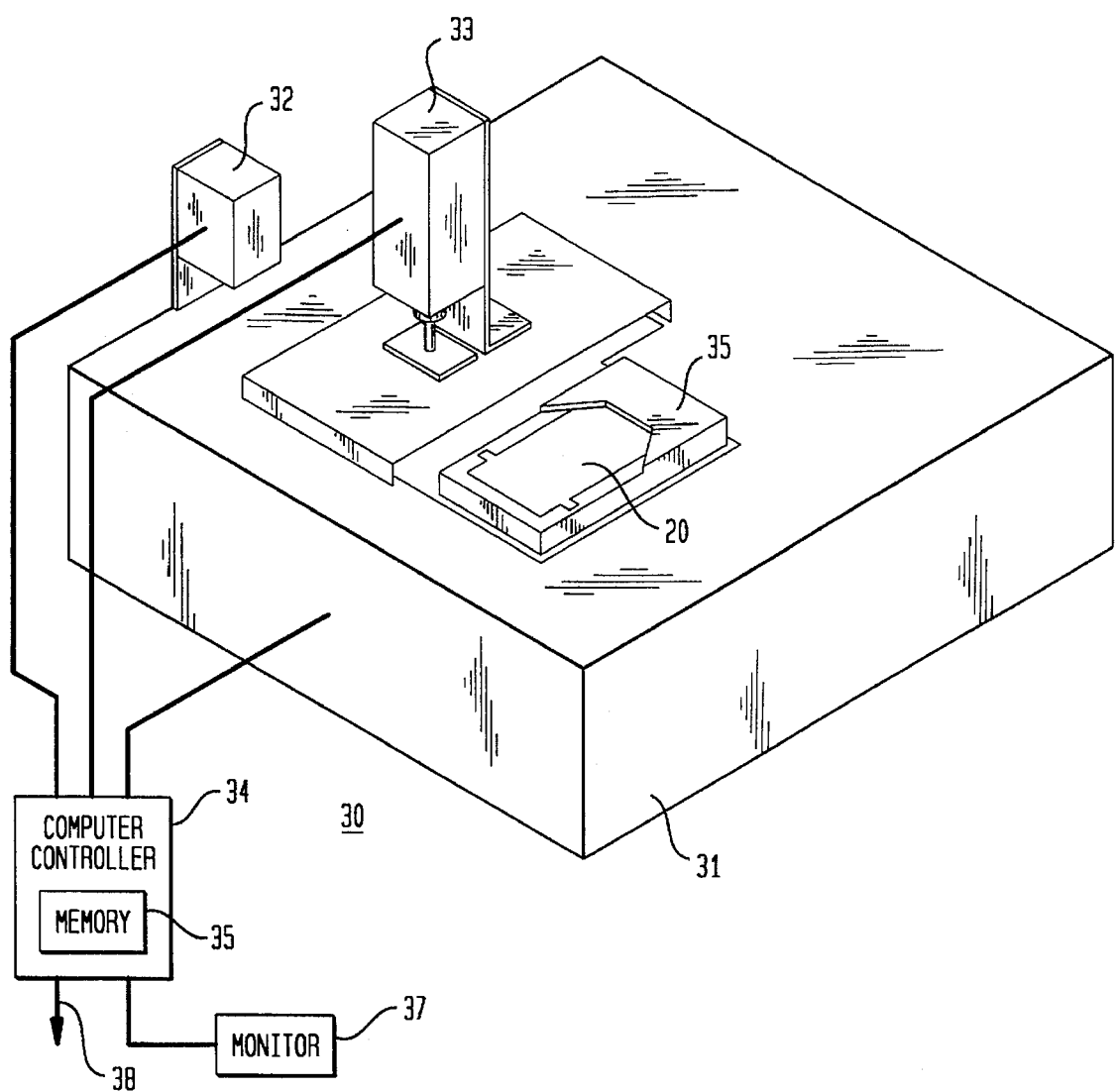
FIG. 3 is a partially isometric and schematic representation of a processing arrangement constructed in accordance with the principles of the invention.

FIG. 3 is a schematic, isometric representation of a specific illustrative embodiment of the invention. As shown, processing arrangement 30 is provided with a chassis portion 31 on which is supported a bar code reader 32 and a punch arrangement 33. Also on the chassis portion is disposed a microtiter plate carrier 35 on which is installed microtiter plate 20 which is described in FIG. 2. The microtiter plate carrier is installed on a controllable x-y platform (not shown) which is contained within chassis portion 31 and which will be described hereinbelow with respect to FIG. 5. Bar code reader 32, punch arrangement 33, and the controllable x-y platform are coupled to a computer controller 34 which contains a memory 35 therein.

Figure 4:
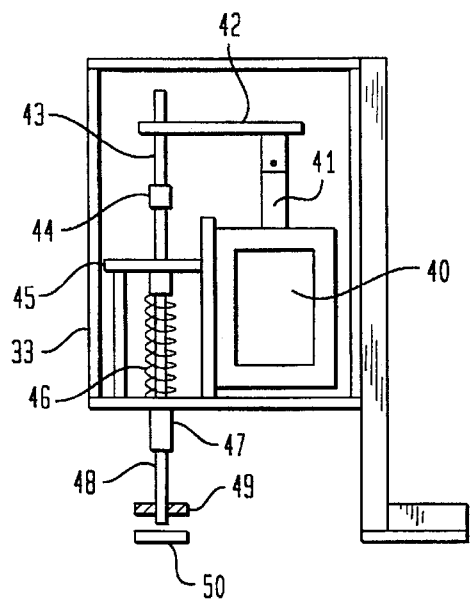
FIG. 4 is a schematic representation of a punch arrangement which is suited for use in the processing arrangement of FIG. 3 for punching specimen samples from the carrier web of FIG. 1.

FIG. 4 is a schematic illustration of punch arrangement 33, showing the internal structure thereof. The punch arrangement is provided with a solenoid 40, which, when activated electrically, causes an armature 41 to be pulled downward. Armature 41 is coupled via a connecting plate 42 to a longitudinally movable shaft 43. As shown, shaft 43 has a collar 44 thereon which limits the longitudinal travel of the shale by stopping against a guide plate 45. It is to be noted that, the invention herein is not limited to electrical actuation of the punch arrangement. Other embodiments of the invention can be configured by persons of skill in the art, which include other arrangements, such as pneumatic or hydraulic drives.

Shaft 43 is maintained in an upward position by operation of a compression spring 46. The shaft is coupled via a coupler 47 to a punch rod 48. Punch rod 48 is engaged with an upper punch plate 49, there is additionally provided a lower punch plate 50. In operation, the item to be punched, such as carrier web 10, is inserted between the upper and lower punch plates, and upon actuation of solenoid 40, the punch rod descends through a hole (not shown in this figure) ion lower punch plate 50, thereby punching a specimen sample out of the carrier web. In a dried blood spot embodiment of the invention, since the dried blood of the carrier web is distributed substantially uniformly, the punched-out specimen sample can be considered to constitute a quantified amount of human sera.

Figure 5:
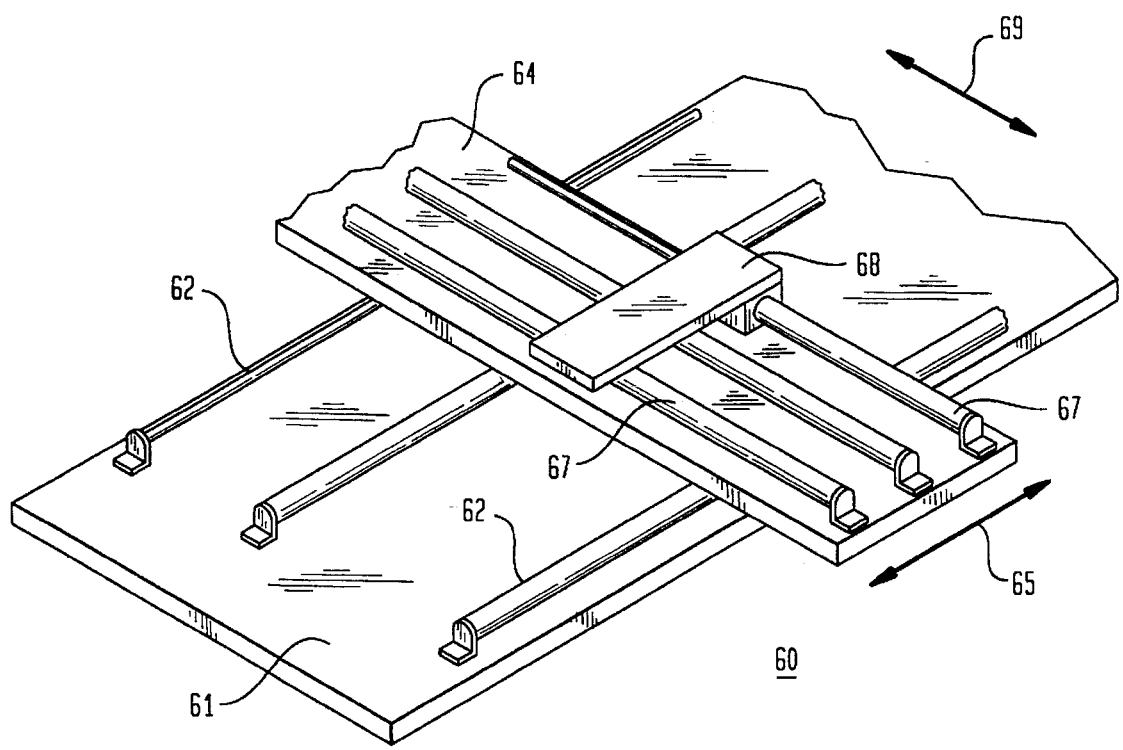
FIG. 5 is a partially fragmented isometric representation of a controllable x-y carrier for moving the microtiter plate of FIG. 2.

As previously noted, microtiter plate carrier plate 35 is installed on the movable platform of controllable x-y platform 60 shown inn FIG. 5. The controllable x-y platform may be of a conventional type, having a base 61 with a pair of guide rails 62 installed thereon. Any of a plurality of commercially available drive arrangements (not shown) can be employed to urge a second base 64 to travel along guide rail 62 in a direction of two-headed arrow 65. Second base 64 has installed thereon a plurality of guide rails 67 on which a carrier platform 68 is urged in a direction of two-headed arrow 69 by any of several commercially available drive arrangements.

Referring once again to FIG. 3, a carrier web (FIG. 1) is manually placed under bar code reader 32, and the identification information obtained therefrom is conducted to computer controller 34 where it is stored in a memory 35. Computer controller 34 causes the controllable x-y platform (FIG. 5) to move microtiter plate carrier 35 thereon such that one of the compartments in microtiter plate 20 is in registration with the punch hole and punch rod of punch arrangement 33. The punched-out specimen sample (not shown) is urged by the punch rod into the predetermined well, or compartment, of microtiter plate 20. This location, as identified by the position information associated with the controllable x-y platform, is stored by the computer controller in the memory. Thus, the computer memory contains information relating to the identification of the carrier web, and the corresponding well in the microtiter plate where the associated specimen sample is deposited. As previously indicated, in order to prevent the specimen sample from leaving the well, as might be the case in environments where there is significant static electricity present, the specimen sample may be cut in a shape or dimension larger than the well, whereby an interference fit is achieved.

The correlation data may be displayed, illustratively as a graphical depiction using the Windows® graphical user interface environment provided by MicroSoft Corporation. In one embodiment of the invention, the information presented on monitor 37 may consist of a depiction of the microtiter plate and the wells therein with information identifying the carrier web from which the specimen samples were obtained set forth in each representation of the predetermined well. Computer controller 34 is additionally provided with a data output port 38 whereby the data is made available to other components (not shown) in a computerized laboratory (not shown).

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A loader arrangement for forming specimen samples from a sample carrier web and loading the specimen samples in a predetermined array of specimen samples, the loader arrangement comprising:

compartment tray means having a plurality of compartments, each of the compartments having an associated compartment opening, said compartment openings being arranged in the predetermined array arrangement, for holding the specimen samples;

punch means for punching out the specimen samples from the sample carrier web, said punch means having a female punch portion arranged on a first plane, said female punch portion having a punch hole therethrough, and a punch rod portion arranged to travel in a first direction of travel through the sample carrier web and said punch hole, whereby a specimen sample is punched out of the carrier web and urged by said punch rod into a predetermined one of said compartment openings of said compartment tray means;

controllable tray carrier means for moving said compartment tray means along first and second axes of motion; and control means for controlling said controllable tray carrier means whereby predetermined ones of said compartment openings are moved into registration with said punch hole of said punch means.

2. The loader arrangement of claim 1 wherein said punched out specimen sample has a size characteristic which is larger than a corresponding size characteristic of said compartment openings, whereby said punched out specimen sample achieves an interference fit in said predetermined one of the compartment openings.

3. The loader arrangement of claim 1 wherein said sample carrier web is provided with a unique identification code, and there is further provided code reader means connected to said control means for conducting sample carrier web identification data to said control means.

4. The loader arrangement of claim 3 wherein control means is provided with a data port for issuing said sample carrier web identification data.

5. The loader arrangement of claim 3 wherein said control means is provided with a memory capacity for storing correlation data corresponding to a correlation of said sample carrier web identification data to compartment location data corresponding to the location of respective compartments in the two-dimensional array of the compartments.

6. The loader arrangement of claim 5 wherein there is further provided graphical interface means for providing a graphical depiction of said correlation data.

7. A loader arrangement for forming specimen samples from a sample carrier web and loading same into a predetermined array configuration, the loader arrangement comprising:

punch means for punching out the specimen samples from said carrier web, said punch means having a punch hole and a punch rod, the punch rod being arranged to travel through the sample carrier web and said punch hole, and thereby punching out a specimen sample from the sample carrier web;

a micro well plate having a plurality of compartments arranged in the predetermined array configuration for receiving respective ones of the punched out specimen samples;

controllable array carrier means for moving the micro well plate along first and second axes of motion substantially orthogonal to the travel of said punch rod; and control means for controlling the motion of said controllable array carrier means whereby a predetermined compartment of the micro well plate is moved into registration with the direction of travel of said punch rod of said punch means, the punched out specimen samples being urged into said compartments of said micro well plates in response to said travel by said punch rod.

8. The loader arrangement of claim 7 wherein there is further provided identification means coupled to said control means for producing a signal which corresponds to the identification of the sample carrier web.

9. The loader arrangement of claim 8 wherein said identification means comprises reader means for reading an identification code on the sample carrier web.

10. The loader arrangement of claim 7 wherein said control means controls the motion of said controllable carrier array means whereby the micro well plate is moved between a first region wherein the predetermined compartment of the micro well plate is moved into registration with said punch hole of said punch means, and a second region wherein the micro well plate is to be replaced.

11. A method of processing specimen samples from a sample carrier web, the method comprising the steps of:
controlling the motion of an array carrier for moving a micro well plate having an array of compartments therein along first and second axes of motion;
punching out a specimen sample from the carrier web with a punch arrangement having a punch hole and a punch rod, the punch rod being arranged to travel through the sample carrier web and the punch hole in a direction of motion substantially orthogonal to the first and second axes of motion of the micro well plate; and urging the specimen sample by means of the punch rod into a predetermined compartment of the micro well plate, the predetermined compartment of the micro well plate being moved into registration with the punch rod during said step of controlling.

12. The method of claim 11 wherein there is further provided the step of repeating said steps of controlling, punching out, and urging for different ones of the compartments of the micro well plate.

13. The method of claim 11 wherein said step of urging comprises the further step of driving the specimen sample into the predetermined compartment of the micro well plate to achieve an interference fit of the specimen sample therein.

14. The method of claim 11 wherein said step of controlling comprises the step of further controlling the motion of the array carrier between a micro well plate loading region and a micro well plate replacement region.

15. The method of claim 11 wherein there is further provided the step of reading a carrier web identification symbol for identifying the carrier web uniquely.

16. The method of claim 15 wherein there is further provided the step of correlating the identity of the carrier web with a respectively associated compartment of the micro well plate.

17. The method of claim 15 wherein said step of reading a carrier web identification symbol comprises the step of reading a bar code printed on the carrier web.

* * * * *